United States Patent [19]

Lindgren

[11] Patent Number: 6,105,714
[45] Date of Patent: Aug. 22, 2000

[54] HEARING PROTECTION DEVICE

[75] Inventor: Mats Lindgren, Vikmanshyttan, Sweden

[73] Assignee: AB Kompositprodukter S.K.-F.M., Vikmanshyttan, Sweden

[21] Appl. No.: 09/297,722

[22] PCT Filed: Nov. 7, 1997

[86] PCT No.: PCT/SE97/01867

§ 371 Date: May 7, 1999

§ 102(e) Date: May 7, 1999

[87] PCT Pub. No.: WO98/20820

PCT Pub. Date: May 22, 1998

[30] Foreign Application Priority Data

Nov. 10, 1996 [SE] Sweden .................................. 9604134

[51] Int. Cl.$^7$ ........................................................ A61B 7/02
[52] U.S. Cl. ........................ 181/135; 181/130; 181/128; 181/126; D24/106; D24/173; D24/174; D29/112
[58] Field of Search ..................................... 181/135, 130, 181/128, 126; D24/174, 173, 106; D29/112; D14/249, 205

[56] References Cited

U.S. PATENT DOCUMENTS

| 1,224,331 | 5/1917 | Smart . | |
|---|---|---|---|
| 2,641,327 | 6/1953 | Balmer . | |
| 3,667,569 | 6/1972 | Mackey et al. | 181/31 R |
| 4,029,169 | 6/1977 | Huntress . | |
| 5,298,691 | 3/1994 | Leight | 181/135 |
| 5,824,966 | 10/1998 | Leight | 181/130 |

FOREIGN PATENT DOCUMENTS

| 1037901 | 10/1990 | France . |
|---|---|---|
| 463064 | 10/1990 | Sweden . |

*Primary Examiner*—Paul Ip
*Assistant Examiner*—Edgardo San Martin
*Attorney, Agent, or Firm*—Sughrue, Mion, Zinn, Macpeak & Seas, PLLC

[57] ABSTRACT

An arrangement in hearing protection devices, headphones and the like of the type comprising a frame (1) and plugs (2) arranged at both ends of the frame. Each of the plugs is pressed into contact with the orifice of the related auditory meatus and may also partly enter the passage. The frame (1) is provided with means (3) that contact the skull bone at the related ear for the purpose of dampening vibrations in the frame. Those means can be shaped like bent or enlarged portions of the frame adjacent to each end thereof, said portions being arranged, when the device is in use, to be held in pressure contact against the skull bone in the area of the respective ear.

8 Claims, 2 Drawing Sheets

HEARING PROTECTION DEVICE

BACKGROUND OF THE INVENTION

The present invention relates to an arrangement in hearing protection devices, head phones and the like, comprising a generally U-shaped frame having plugs at its both ends, which plugs by the frame are pressed into contact with the orifices of the auditory meatus.

While the invention will below be described in connection with a hearing protection device, it may also, as mentioned above, be utilized e.g. in connection with head phones and the like suffering from problems similar to those occurring in hearing protection devices and accounted for below.

A most widely used type of hearing protection device consists of a U-shaped frame, at each of its two ends equipped with soft plugs which by the frame are pressed into sealing engagement with the orifices of the auditory meatus. The plugs may be shaped so that a portion thereof slightly enters the passage. In order to match the irregular shape of the passage the plugs are generally manufactured in a soft rubber or plastic material. The frame generally consists of a relatively stiff plastic material in order to create a suitable, resilient force pressing against the plugs in order to attain an efficient sealing between each of them and related passage orifices. In this way one achieves a good damping of sounds from ambient noise sources.

However, this type of hearing protection device suffers from a disadvantage in that the frame may itself generate undesired noise, namely if hit by or brought into rubbing contact with another object. As the frame is usually located under the chin or around the back of the head this may occur at movements of the head causing e.g. a necklace to hit the frame or the frame to just scrape along an article of clothing, e.g. a shirt collar.

When the frame is affected mechanically, vibrations are generated therein, i.a. in the form of axial oscillations in the direction of the adjacent plug. Because of the soft material in the plug those oscillations are not dampened to any appreciable extent. While the amplitude of the frame and plug movements is small they will, i.a. in consequence of the small volume of air between the plug and the tympanic membrane, result in sound-generating pressure variations in the hearing passage which cause sound pressure.

SUMMARY OF THE INVENTION

The main object of the present invention is to improve hearing protection devices of the kind above mentioned in order to substantially dampen the noise generated upon contact between an alien article and the frame of the hearing protection device.

The invention is based on the realization that such a damping can be attained if the vibrations in the frame generated upon contact with an alien object are dampened before they reach the plugs pressed against the orifices of the auditory meatus.

In accordance with the present invention the above mentioned object is obtained by means of a device of the type defined in the first paragraph of this specification, which is characterized in that said frame is equipped with means such as an element that contacts the skull bone adjacent each ear for the purpose of dampening vibrations in said frame.

Due to the contact between the element and the skull bone, the vibrations in the frame will be dampened before they reach the plugs mounted at the ends of the frame. This results in a substantial reduction of the sound pressure which those vibrations would otherwise generate.

The means used to obtain the damping may be constituted by a bent portion of the frame adjacent to each of its two ends, said portions being arranged, when the device is in use, to be held pressed against the bone in the skull adjacent to the related ear.

The bent portions are suitably shaped so that the frame can be positioned below the chin or around the back of the head of the carrier, the contact between said portions and the skull bone being upheld.

As an alternative the means arranged to dampen the vibrations in the frame can be constituted by enlarged portions of the frame proper or by elements attached thereto, those portions or elements being arranged during use of the device to be pressed against the skull bone in the area of the adjacent ear. The plugs, intended to be held in pressure contact with the orifices of the auditory meatus, are then suitably mounted at the free end of a short arm, the opposite end of which is connected to said portions.

The arms can be rotatably and also devibrationally connected to said portions or elements. Further, they are suitably formed so that the frame can be placed below the chin or around the back of the head of the carrier in response to his own choice.

BRIEF DESCRIPTION OF THE FIGURES

The invention will now be described in greater detail, reference being made to the exemplifying embodiments thereof shown on the enclosed drawings.

DETAILED DESCRIPTION OF THE PREFERRED EMBODIMENTS

Figure 1:
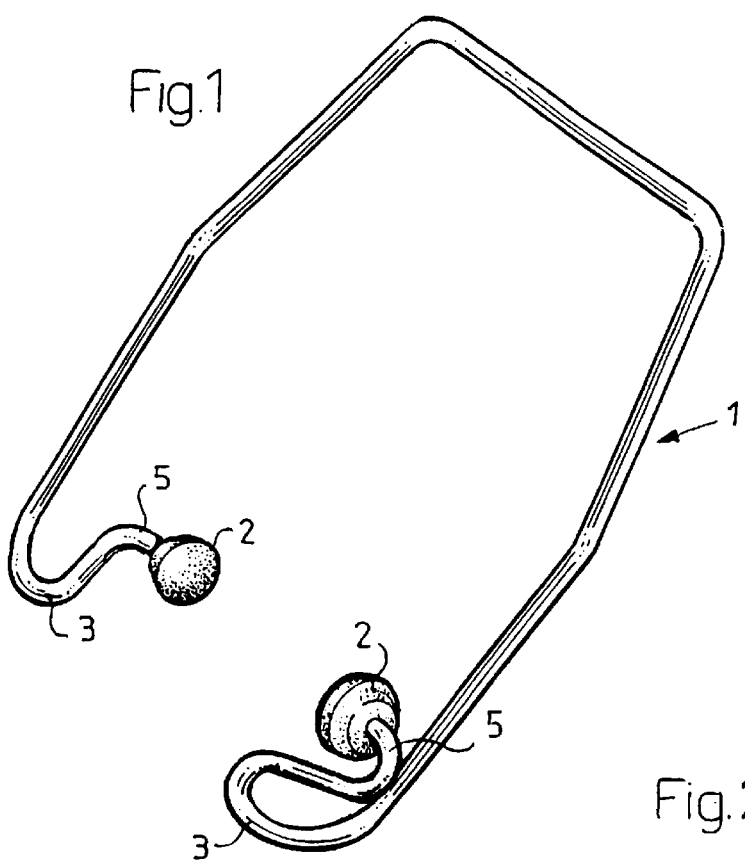
FIG. 1 shows a hearing protection device according to a first embodiment of the invention.

In FIG. 1 reference numeral 1 indicates a frame of a hearing protection device, said frame being manufactured from a relatively rigid plastic material. At each of the two free ends of the U-shaped frame 1 there is mounted a plug 2 of a soft rubber or plastic material. Due to the stiff resilience of the frame 1, plugs 2 are brought into pressure contact with the orifice of the related auditory meatus. Each leg of the frame is near its plug 2 provided with a bent portion 3 directed inwards and backwards in relation to the plane of the drawing paper.

Figure 2:
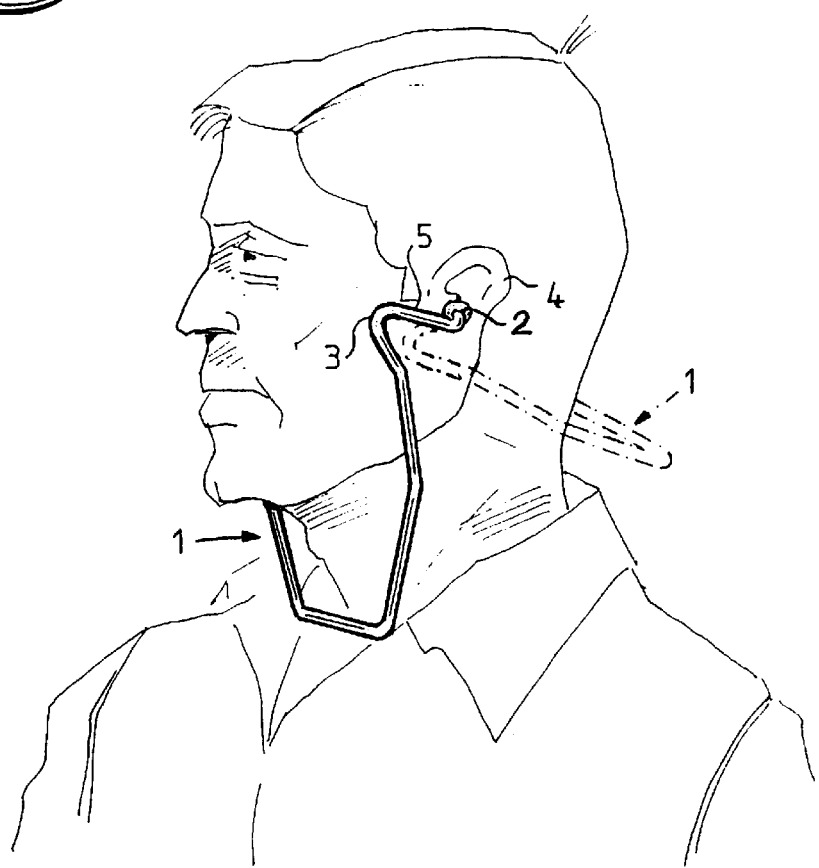
FIG. 2 illustrates the device of FIG. 1 shown in two different operational positions.

When in use the device can be positioned as illustrated in FIG. 2, so that the frame either passes below the chin or behind the back of the head as shown in phantom. If the legs are sufficiently long the central part of the frame may alternatively pass over the top of the head. Due to the double bent shape of portion 3 that portion will in both cases, cf. FIG. 2, contact the skull bone immediately in front of the ear 4. Between portion 3 in contact with the skull bone and the related plug 2 there is only a short arm 5 running just a small risk to get into contact with any alien object. The length of the arm 5 may be 1–5 cm.

In contrast thereto, the part of frame 1 located outside portion 3 may come into contact with other objects which would then cause vibrations in the frame. When the frame is shaped as shown, those vibrations will to a substantial extent be dampened due to the contact between frame portion 3 and the skull bone, meaning that they are not propagated to plug 2 closing the auditory meatus. In this way there is achieved an elimination or substantial reduction of the noise which the vibrations in the shanks of frame 1 would otherwise generate.

Figure 3:
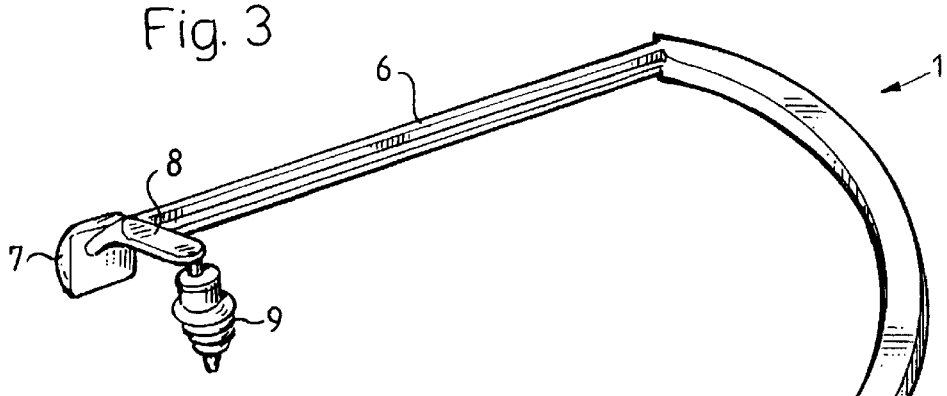
FIG. 3 shows a second embodiment of a hearing protection device according to the invention.

In FIG. 3 there is shown a second embodiment of the invention in which the shanks 6 of frame 1 at their free ends exhibit enlarged portions 7 having a curved, essentially hemispherical shape. Attached to the portions 7 are the one ends of short, bent arms 8, the opposite ends of which carry the ear plugs 9. The intended function of those plugs is to seal off the orifice of the auditory meatus and, at the same time, also slightly to enter that passage in order further to improve the sealing effect.

Figure 4:
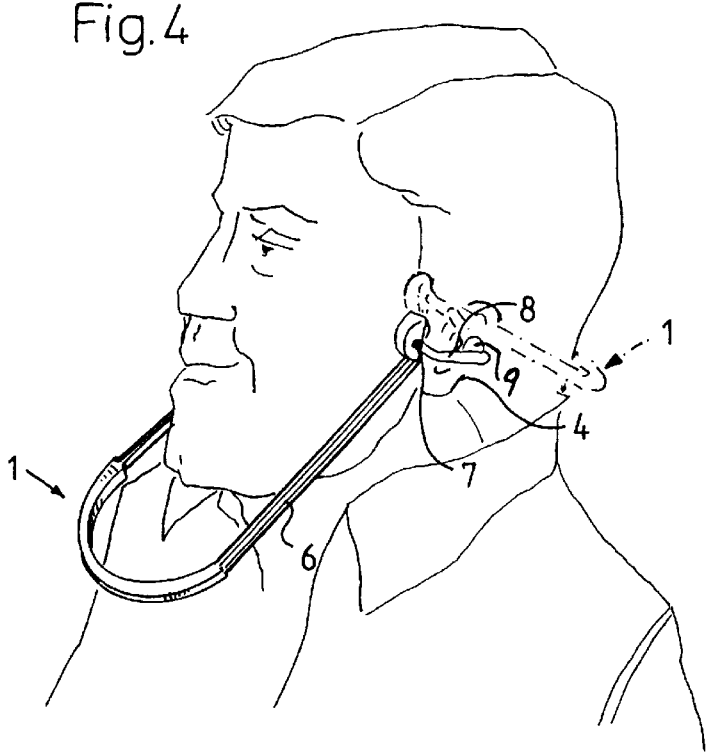
FIG. 4 illustrates the device of FIG. 3 shown in two different operational positions.

In the use of this device the enlarged portions 7 will be resiliently pressed into contact with the skull bone in the area close to the ear, reference being made to FIG. 4. The arms 8 and the shanks of the frame are shaped so that this will apply irrespective of whether the frame is located below the chin or around the back of the head. The arms 8 may also be dimensioned so as to permit the frame to pass on top of the head.

Figure 3A:
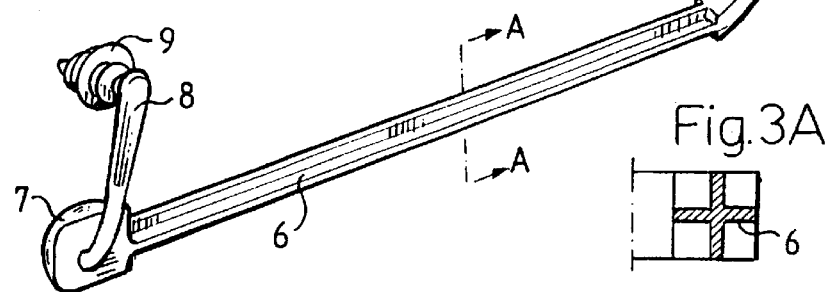
FIG. 3A is a section along line A—A in FIG. 3.
Figure 3A:

When the device is in use, it may become necessary slightly to twist the shanks 6 which, however, should exert the force necessary to maintain the plugs 9 in pressure contact with the orifice. To that end the shanks 6 may be given a cruciform cross-section, see FIG. 3A. Such shanks do essentially retain their bending resistance, the torsional resistance being simultaneously reduced.

Vibrations in the shanks 6 which are caused by frame 1 colliding with some external article will be dampened in the same way as described above thanks to the contact between the enlarged portions 7 and the skull bone. Accordingly, no appreciable sound-generating vibrations will be transferred to the plugs 9 via the short arms 8.

A feature common to both of the embodiments above described is that the bent portions 3 and the curved portions 7 offer a soft contact against the skull bone independently of the position assumed by the frame. The point of contact will vary somewhat as a function of whether the frame is located below the chin, around the back of the head or above the head. The described contact between the frame and the skull bone also provides that the plugs cannot move relative to the ear passage with the same ease as when the frame does not make any such contact. This means that another source of noise disturbing the carrier is reduced.

As an alternative to providing the shanks of frame 6 with the enlarged portions shown in FIG. 3 separate elements can be attached to the free ends of the shanks 6. In that case a devibrating material can be located between the shanks and those elements. In a corresponding manner the short arms 8 may be devibratedly connected to the portions 7 so that they counteract vibration propagation to the plugs 9. The enlarged portions 7 or the corresponding separate elements, respectively, should consist of a homogeneous material, preferably a plastic material such as an acetal or polypropylene, capable of transmitting to the skull bone the vibrations in the shanks 6.

The invention has above been described with reference to the two embodiments shown in the drawing. It can, however, be modified in several respects within the scope of the claims. Consequently, the shape of the frame, the shanks, the plugs and the connecting arms can be changed in many different ways without any deviation from the characteristic novelty of the invention, namely the presence of a point of contact between each frame shank and the skull bone. The position of that contact point shall be between each plug and that portion of the frame which may come into a vibration-generating contact with another article. While in the drawing that point has been shown located in front of the ear, the shanks of the frame and the arms carrying the plugs may equally well be designed so that the contact point will be positioned behind or above the ear.

What is claimed is:

1. A hearing protection device, comprising:
   a) a generally U-shaped frame (1) having ear plugs (2; 9) at opposite ends thereof, said plugs adapted to be pressed by the frame into contact with the orifices of the auditory meatus, wherein
   b) said frame includes means (3; 7) held in direct contact with the cheek bone of the skull both in front of and adjacent each ear (4) to dampen vibrations generated in said frame and prevent noise resulting therefrom from reaching said plugs.

2. A device as claimed in claim 1, wherein said means are constituted by a bent portion (3) of the frame (1) adjacent to each of its two ends, said portions being arranged, when the device is in use, to be held pressed against the skull bone adjacent the related ear.

3. A device as claimed in claim 2, wherein the portions (3) of the frame (1) in contact with the skull bone are curved.

4. A device as claimed in claim 2, wherein said bent portions (3) are shaped so as to permit positioning of the frame below the chin or around the back of the head of the wearer.

5. A hearing protection device, comprising:
   a) a generally U-shaped frame (1) having ear plugs (9) at opposite ends thereof, said plugs adapted to be pressed by the frame into contact with the orifices of the auditory meatus, wherein
   b) said frame includes means (7) held in direct contact with the skull bone both in front of and adjacent each ear (4) to dampen vibrations generated in said frame and prevent noise resulting therefrom from reaching said plugs,
   c) said means are constituted by enlarged portions of the frame,
   d) each of the plugs to be brought in pressure contact with the orifice of the related auditory meatus is mounted at the free end of a short arm (8), the opposite end of which is connected to the related portion, and
   e) said arms are devibrationally mounted at said portions.

6. A device as claimed in claim 5, wherein the surface of said portions (7) or elements facing the skull exhibit a curved shape.

7. A device as claimed in claim 5, wherein said arms (8) are rotatably mounted at said portions (7) or elements.

8. A device as claimed in claim 5, wherein said short arms (8) are shaped so as to permit location of the frame (1) below the chin or around the back of the head of the wearer.

* * * * *